United States Patent [19]

Milberger

[11] 4,099,923
[45] Jul. 11, 1978

[54] AUTOMATIC CATALYTIC SCREENING UNIT

[75] Inventor: Ernest C. Milberger, Solon, Ohio

[73] Assignee: The Standard Oil Company, Cleveland, Ohio

[21] Appl. No.: 760,198

[22] Filed: Jan. 17, 1977

[51] Int. Cl.² .................... G01N 31/08; G01N 31/10
[52] U.S. Cl. .............................. 23/254 R; 23/253 PC; 23/255 R
[58] Field of Search ........ 23/230 PC, 253 PC, 254 R, 23/230 R, 253 R, 259

[56] References Cited

U.S. PATENT DOCUMENTS

| | | | |
|---|---|---|---|
| 2,753,246 | 7/1956 | Shields et al. | 23/253 PC |
| 3,414,382 | 12/1968 | Kapff et al. | 23/253 PC |
| 3,864,083 | 2/1975 | Green | 23/253 PC |
| 3,969,081 | 7/1976 | Jackson | 23/284 |

Primary Examiner—R.E. Serwin
Attorney, Agent, or Firm—Herbert D. Knudsen; John E. Miller, Jr.

[57] ABSTRACT

An automatic catalyst screening unit for determining if one or more potential catalysts exhibits significant catalytic activity for a particular chemical reaction comprising a reactor module defining a plurality of elongated reaction chambers for receiving respective potential catalysts; feeding means for individually and selectively feeding each of the reaction chambers with gaseous reactant; and analyzing means for analyzing the product passing out of the reaction chambers, the analyzing means communicating with the plurality of reaction chambers by means of a common manifold.

20 Claims, 3 Drawing Figures

AUTOMATIC CATALYTIC SCREENING UNIT

BACKGROUND OF THE INVENTION

The present invention relates to a process and apparatus for automatically screening catalysts to discover new catalysts useful for various catalytic reactions.

In the art of catalysis, there is little predictability between the composition and/or structure of a material and its catalytic properties. Therefore, essentially the only way to determine if a particular material is a good catalyst is by testing the material under the actual conditions encountered in the process of interest. When it is desired to discover a new catalyst useful for a particular reaction, large groups of different materials are each individually tested and those failing to show a predetermined minimal activity for the conversion of the starting material to the desired end product are screened out.

In the ongoing search for better catalysts for known reactions, one of the most time consuming jobs is the methodical screening of different potential catalysts. If this task could be automated so as to run without the aid of operating personnel during weekends and overnight, not only would the search for new catalysts be speeded up but also available manpower could be utilized on other work.

Accordingly, it is an object of the present invention to provide an automated catalyst screening apparatus which is capable of subjecting a plurality of different catalysts to predetermined activity tests without the aid of operating personnel on an automatic basis.

It is another object of the present invention to provide an automated catalyst screening apparatus as described above which is simple in construction, inexpensive to build and constructed so as to minimize down time because of problems with hardware.

SUMMARY OF THE INVENTION

These and other objects are accomplished in accordance with the present invention which provides an automatic catalyst screening unit which can be filled with a plurality of different potential catalysts and programmed to individually test each catalyst for catalytic activity in a particular chemical reaction under varying operating conditions.

Thus, the present invention provides an automatic catalyst screening unit which takes the form of a reactor module defining a plurality of elongated reaction chambers for receiving respective potential catalysts; feeding means for individually and selectively feeding each of the reaction chambers with gaseous reactant; and analyzing means for analyzing the product passing out of the reaction chambers, the analyzing means communicating with said plurality of reaction chambers by means of a common manifold.

More specifically, the present invention provides an automatic catalyst screening unit comprising a reactor module comprising means defining a plurality of chambers having essentially equal volumes for receiving respective potential catalysts, each of the chambers having an inlet and an outlet; first heating means for heating the potential catalysts when received in the chambers to the same temperature; first control means for controlling the first heating means; feeding means for feeding gaseous reactant to the plurality of chambers; selector valve means intermediate the feeding means and the plurality of chambers for selectively placing only one of the chambers in fluid communication with the feeding means at any one time; analyzing means for analyzing gross product passing out of the plurality of chambers; means defining a common manifold attached to the outlets of the plurality of chambers; and second control means for controlling the first control means, the selector valve means and the analyzing means so that (1) the gaseous reactant is individually and sequentially fed to the plurality of chambers in a predetermined sequence at at least one predetermined temperature and (2) reaction product passing out of each chamber is fed to the analyzing means via the common manifold means and analyzed for useful product.

In addition, the present invention also provides a novel reactor module for testing a plurality of potential catalysts comprising an essentially solid block; an elongated heating element received in and integral with the block, the block defining a plurality of elongated, essentially parallel, reaction chambers arranged in annular configuration around the elongated heating element; and means defining a common manifold in fluid communication with each of said reaction chambers.

Once the inventive automatic screening unit has been charged with potential catalyst and the flow rates of one or more reactant gases set, the inventive automatic screening unit will operate automatically, testing each of the potential catalysts at one or more different temperature levels for catalytic activity. Because of its automatic operation, a great deal of personnel time is saved. Also, because of its simplistic design, down time due to hardware difficulties is essentially eliminated. Nonetheless, the analysis generated by the automatic screening unit is still sufficient to indicate which potential catalysts show promising possibilities and hence should be further investigated and which potential catalysts can be discarded from consideration. Thus, the inventive automatic screening unit serves as a valuable research tool since it makes possible a rough screening of potential catalysts at very low cost and with great savings of time.

DETAILED DESCRIPTION

The inventive automatic catalyst screening unit is intended to provide a rough screening of potential catalysts. In other words, the inventive automatic catalyst screening unit is not intended to develop dispositive or even reasonably thorough data regarding the catalytic properties of a particular catalyst. Rather, it is a function of the inventive automatic catalyst screening unit to provide a preliminary indication that a potential catalyst either does or does not have sufficient catalytic activity and the right type of catalytic activity to warrant further investigation of its properties. To this end, the inventive automatic catalyst screening unit has been designed to provide a relatively simple analysis of the reaction product of each testing run but an analysis which nonetheless provides sufficient information for those skilled in the art to weed out obviously unsuitable materials. Furthermore, the inventive automatic catalyst screening unit has been designed to have wide versatility so that it can be employed to test potential catalyst for use in a wide variety of different chemical reactions.

To this end, it is contemplated that the inventive automatic catalyst screening unit can be employed on a wide variety of different chemical reactions in which the reactants are fed to the catalytic reactor in the form of gases. Processes including oxydehydrogenation, for example oxydehydrogenation of butenes to butadiene, $C_4$ hydrocarbons to maleic anhydride, and propylene to acrolein) ammoxidation processes (for example, the ammoxidation of propylene or isobutylene with ammonia and air to form acrylonitrile and methacrylonitrile, respectively) and dehydrogenation processes can be tested with the catalyst screening unit of the present invention.

Of particular interest are those processes in which a hydrocarbon is catalytically reacted either alone or in the presence of oxygen or ammonia or both. Therefore, in the preferred embodiment, the inventive catalyst screening unit is designed to include means for supplying hydrocarbon, means for supplying an oxygen-containing gas (e.g. air) and means for supplying ammonia. Depending on the type of reaction being studied, all of these supply means can be operational or, if appropriate, the means for supplying air and/or the means for supplying ammonia can be shut down. Because of the wide variety of different chemical processes using these three ingredients, however, the inventive catalyst screening unit when equipped with means for supplying these different gases is very versatile and can be used to screen catalysts for a wide variety of different chemical reactions.

Figure 1:
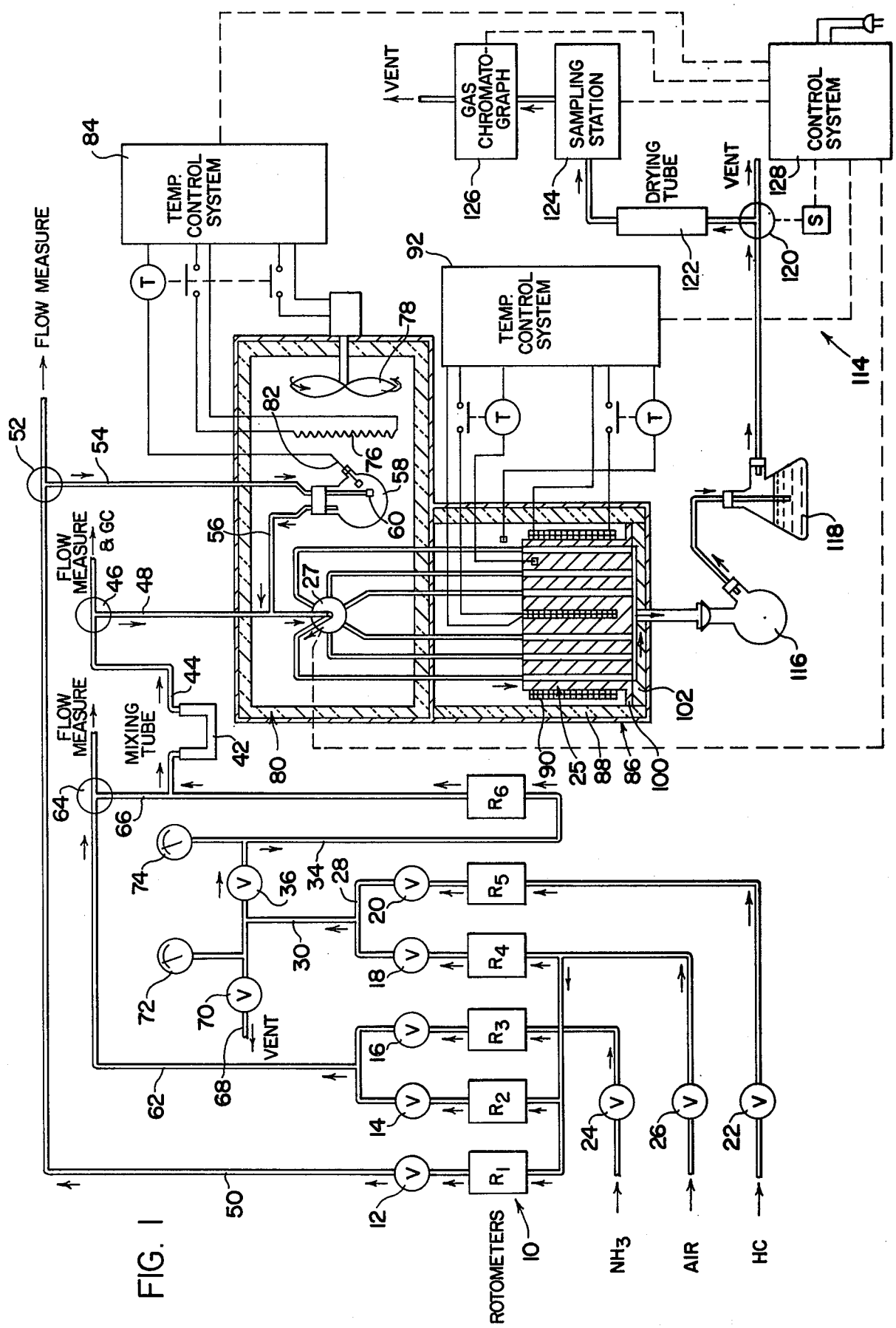
FIG. 1 is a schematic flowsheet of the automatic catalyst screening unit of the present invention.

Turning now to the drawings, the flow system of the preferred embodiment is illustrated in FIG. 1. A reactant feeding means generally indicated at 10 takes the form of a plurality of flow measuring means $R_1$, $R_2$, $R_3$, $R_4$ and $R_5$ (rotometers in the specific embodiment) and associated valves 12 to 20, respectively. Attached to the inlet of rotometer $R_5$ via valve 22 is a hydrocarbon source, and attached to the inlet of rotometer $R_3$ via valve 24 is an ammonia source. Similarly, a source of air is attached via valve 26 to parallel-arranged rotometers $R_1$, $R_2$ and $R_4$.

Contact of the gaseous reactants with the prospective catalysts occurs in a reactor module generally indicated at 25. In the specific embodiment illustrated, reactor module 25 contains six separate elongated reaction chambers for receiving catalysts and carrying out the catalytic reaction. In order to feed each of the separate reaction chambers with gaseous reactants in accordance with a predetermined time sequence, a six-way valve 27 is provided. Hydrocarbon passing out of rotometer $R_5$ is transferred to selector valve 27 via a hydrocarbon flow path defined by conduit 28, conduit 30, valve 36, conduit 34, rotometer $R_6$, mixing tube 42, conduit 44, three-way valve 52 and conduits 54 and 56. Ammonia is supplied to selector valve 27 by an ammonia flowpath taking the form of valve 16, conduit 62, three-way valve 64, conduit 66, mixing tube 42, conduit 44, three-way valve 46 and conduit 48.

In order to provide a source of water vapor in the reactant gas fed to reactor module 24, beaker 58 is provided. Air passing out of end 60 of conduit 54 takes up water vapor as it bubbles through the water in beaker 58 on its way to conduit 56. Content of the amount of water taken up by the air is accomplished by controlling the temperature of the water in beaker 58 in the manner discussed below.

In normal operation of the inventive automatic catalyst screening unit, the flow rates of ammonia and hydrocarbon are very small, i.e. on the order of 4 cc's per minute for hydrocarbon and 20 cc's per minute for ammonia in the preferred embodiment. Since it is difficult to measure and control such small gas flows, air is mixed with the ammonia and the hydrocarbon passing out of rotometers $R_3$ and $R_5$, respectively, so that the flow of gas through the hydrocarbon flowpath and the ammonia flowpath are larger. To this end, rotometers $R_2$ and $R_4$ with associated valves 14 and 18, respectively, are provided, these rotometers being arranged in parallel with rotometer $R_1$. Suitable amounts of air are allowed to flow through the rotometers $R_2$ and $R_4$ for increasing the gas flow through the ammonia flowpath and hydrocarbon flowpath, respectively. By directly comparing the readings on rotometers $R_2$ and $R_3$, the relative amounts of ammonia and air in the gas flowing through the ammonia flow-path can be determined. Similarly the relative amounts of air and hydrocarbon flowing through the hydrocarbon flowpath can be directly determined by comparing the readings on rotometers $R_4$ and $R_5$.

In order to facilitate control of the hydrocarbon flow rate, vent conduit 68 having an associated valve 70 and pressure gauge 72 is attached to the hydrocarbon flowpath upstream of valve 36. Since it is very difficult to accurately measure very low hydrocarbon flow rates with normal gauge-type flow measuring devices such as rotometers and the like, the present invention adopts a system whereby a large majority of the gas from rotometers $R_4$ and $R_5$ passing through the hydrocarbon flowpath is discharged to waste and only a small amount transferred to reactor module 25, the so-called "split feed" systems. To this end, vent conduit 68 and associated valve 70 and pressure gauge 72 as well as valve 36 and pressure gauge 74 are provided. By suitably adjusting valve 70 and 36 and monitoring the gas pressures in pressure gauges 72 and 74 the relative amount of gas passed to reactor module 25 can be accurately controlled even when the total hydrocarbon flow to module 25 is extremely small.

Prior to reaching reactor module 25, the reactant gas or gases are heated to a predetermined elevated temperature. This is accomplished by means of electric heating element 76 and fan blade 78. As shown in FIG. 1, heating element 76, fan blade 78 as well as beaker 58 and selector valve 27 are housed in a common constant temperature box 80, the walls of which are provided with suitable insulation. A temperature sensing device 82 is provided for monitoring the temperature of the water in beaker 58 and this information is fed to a temperature control system 84 which controls heating element 76 so that the temperature within constant temperature box 80 is maintained at a predetermined value.

Immediately below constant temperature box 80 is reactor module 25. Reactor module 24 is housed in heater box 86 which is integral with constant temperature box 80 and which contains a layer of thermal insulation 88 and a cylindrical resistance heating element 90 for heating reactor module 25 to the desired temperature. A temperature control system 92 is provided for sensing the temperature of thermal insulation 88 and controlling the temperature of resistance heater 90. Reactor module 25 is provided within its interior with a second resistance heater which is also controlled by temperature control system 92.

Figure 2:
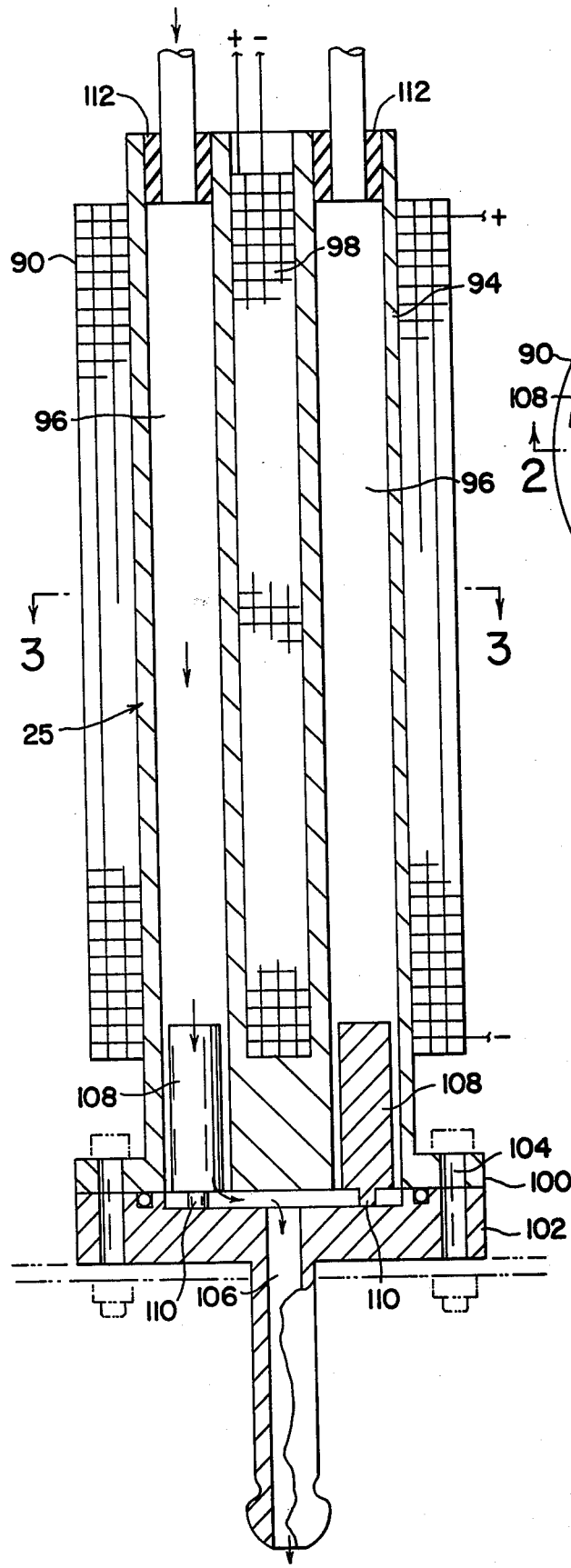
FIG. 2 is a cross-sectional elevational view of the reactor module of the inventive automatic catalyst screening unit.
Figure 3:
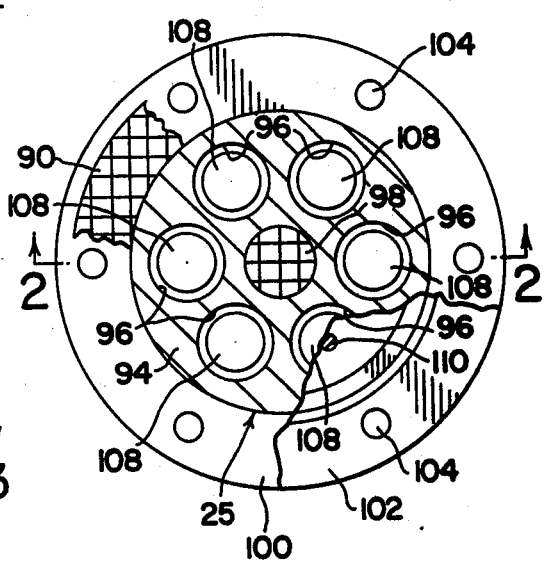
FIG. 3 is a cross-sectional view taken on line 3—3 of FIG. 2.

The structure of reactor module 25 is more thoroughly illustrated in FIG. 2 which is an axial cross-section and FIG. 3 which is a radial cross-section. In the specific embodiment illustrated, reactor module 25 comprises a solid stainless steel block 94 having six cylindrical reaction chambers 96 uniformly spaced about the axial center of block 94. Thus it will be noted that reaction chambers 96 are parallel and arranged in annular configuration about the center of the block. An elongated heating element 98 which is received in and integral with block 94 serves to heat reactor module 25 from the inside thereof. As indicated above, elongated heating element 98 is controlled by temperature control system 92.

Depending about the bottom of block 94 is flange 100 which is provided for attaching outlet connection 102 to block 94. A system of holes 104 is provided in both flange 100 and outlet connection 102 for attaching the two together.

As shown in FIG. 2, outlet connection 102 defines a manifold 106 which is in constant fluid communication with each of reaction chambers in block 94. A removable deadman 108 is received in each of chambers 96 for supporting catalyst charged therein. Depending from the bottom of each of deadman 108 is pin 110 which supports each deadman 108 in place so that clearance is assured for passage of gases into common manifold 106. Sleeves 112 are received in and integral with the upper portions of hole 96 for receiving the conduits attached to selector valve 27. In the embodiment shown, chambers 96 are large enough to accommodate catalyst charges of about 20 cc's with a small plug of quartz wool above and below each catalyst charge.

The gross reaction product passing out of each of reaction chambers 96 passes through common manifold 106 and then into the analyzing system of the inventive apparatus generally indicated at 114. This analyzing system takes the form of a knockout pot 116 for separating solid and liquid components from gaseous reaction product, water scrubber 118 for removing water soluble gases from the product gas, solonoid actuated three-way valve 120, drying tube 122, conventional sampling station 124 and gas chromatograph 126. Since each test run with each respective catalyst must be allowed to proceed for a reasonable period of time (e.g. one hour) so that steady state conditions are reached or at least approached before a sample is taken, solonoid actuated valve 120 is provided to automatically discharge to waste gaseous product obtained before the sampling operation.

The inventive automatic catalyst screening unit is provided with a control system for controlling the operation of the apparatus. This control system, schematically illustrated at 128 controls the operation of selector valve 27, temperature control system 84, temperature control system 92, solonoid actuated valve 120, sampling system 124 and gas chromatograph 126. With this control, the inventive screening unit can be programmed to subject each of the potential catalysts charged into the reactor module to one or a series of catalyst activity tests at the same or different temperatures. For example, in the preferred mode of operation, the six different catalysts charged into the reactor module are each subjected to three different catalytic activity tests at predetermined low, moderate and high temperatures, 18 different test runs being conducted in all.

In order to operate the inventive catalyst screening unit, different potential catalysts are first charged into the six reaction chambers 96 of reactor module 25. This is conveniently done through the bottom of block 94 since outlet connection 102 and dead man 108 are removable from block 94.

Next, the gaseous reactant flow rates are adjusted to the desired values. In the specific embodiment illustrated, this is done manually by the following procedure: The primary air flow through rotometer $R_1$ is established by opening valves 26 and 12. In order to obtain accurate measurement, the primary air stream is bypassed via valve 52 to a suitable flow measuring device such as a soap bubble meter. Once the flow is accurately determined by the bubble meter, rotometer $R_1$ is thereby calibrated and valve 52 is then set so that the primary air passes through conduit 54 to selector valve 27.

The ammonia flow rate is established by adjusting valves 24, 14 and 16 so that ammonia and air flow through rotometers $R_3$ and $R_2$, respectively in a suitable proportion, e.g. 1:1. The actual ammonia flow rate is then measured by diverting the combined air/ammonia stream via valve 64 to an appropriate measuring device. For example, such a measuring device can consist of a stirred dilute hydrochloric acid solution in a vessel equipped with a sintered glass dispersion tube. The ammonia/air stream is bubbled through this solution to a methyl purple end point, or passed the end point with a subsequent back titration. From the normality of the acid and the time of gas flow, the ammonia weight can be calculated and hence rotometer $R_3$ calibrated. The accompanying air flow rate in this combined gas stream can be measured with a soap bubble meter via valve 64 with valve 16 shut off.

The hydrocarbon flow rate is established by opening valve 22 and suitably setting valves 18, 20, 70 and 36 so that 15 to 20% of a hydrocarbon/air mixture in a suitable proportion, e.g. 5 to 15% hydrocarbon, is split off into conduit 34 while the bulk of the hydrocarbon/air mixture is discharged to waste via conduit 68. Generally, this is done by allowing all of the hydrocarbon/air mixture to flow through vent conduit 68 and then opening valve 36 so that a small amount of the flow is split off to conduit 34. If the valves are set so that back pressure valve 72 registers 6 psig and fore pressure valve 36 registers 3 psig, the desired splitting off will be obtained. The hydrocarbon/air mixture split off into conduit 34 after being mixed in mixing tube 42 is diverted via valve 46 to a flow measuring means such as a soap bubble meter to measure the total flow. Also, a sample of the gas is transferred to the gas chromatograph for determining the mole percent hydrocarbon therein. From this data, the hydrocarbon and air flow rate can be calculated and hence rotometers 4, 5 and 6 calibrated.

Once the flow rate of the reactant gases have been manually adjusted, control system 128 is then programmed for the desired reaction conditions. Since the activity of most catalysts is temperature dependent, it is desirable to test each potential catalyst at three different temperatures. Therefore, control system 128 is programmed in accordance with the preferred embodiment to subject each catalyst to activity test runs at a first temperature, a second higher temperature and then a third still higher temperature. From experience it has been found easier to test all catalysts at one temperature before changing the reactor temperature, and so control system 128 is preferably programmed in this manner.

When control system 128 is activated, the operation of the inventive screening unit is completely automatic. Selector valve 27 selects one reaction chamber for receiving the incoming reactant gases in accordance with the command from control system 128, and all incoming reactant gases are fed to this reaction chamber. Control system 128 commands temperature control systems 84 and 92 to maintain the temperatures of constant temperature box 80 and heater box 86 to predetermine values so that the test run can be accomplished at a preselected temperature. Gross reactant passing out of reactor module 25 is separated into gaseous and nongaseous components and the gaseous components pass through water scrubber 118 for removal of water soluble components. In order to allow the reaction in reactor module 25 to come to or at least approach steady state, the reaction is allowed to proceed for a predetermined period of time before the sampling procedure begins. To this end, control system 128 commands solonoid actuated valve 120 to vent the reaction gas for a predetermined period of time until the analyzing procedure begins. When the analyzing procedure begins, control system 128 commands solonoid actuated valve 120 to transfer gaseous reaction product to sampling system 124. Drying tube 122 recovers water vapor from the gaseous reactant product in accordance with known techniques in order to prevent damage to the gas chromatograph. After gaseous reaction product has flowed through sampling system 124 for a short period of time, control system 128 commands sampling system 124 to recover a sample of predetermined volume and transfer this sample to gas chromatograph 126. The sample is then analyzed by gas chromatograph 126 upon command of control system 128 to yield the desired analysis.

After the sample is recovered by sampling system 124 as described above, control system 128 commands selector valve 126 to transfer incoming gaseous reactant to a different reaction chamber. The same procedure for recovering a sample is then followed and a second sample is recovered and analyzed. The same procedure is again repeated until all six catalysts have been tested. At this time, control system 128 then commands temperature control system 92 to increase the temperature of reactor module 24 to a second predetermined temperature. A series of six test runs are then repeated in the manner discussed above.

The inventive catalyst screening unit finds greatest use in testing potential catalysts in processes which utilize normally gaseous feeds such as those utilizing light hydrocarbons. Processes which produce products which can be easily recovered by the knockout pot/scrubber recovery arrangement of the inventive apparatus (i.e. solids, liquids and gases which will dissolve in a solvent or can be absorbed on an absorbent) are especially preferred. For example, it has been found that the inventive catalyst screening unit can be used to great advantage in the screening of catalysts used for the catalytic oxidation of butadiene with oxygen to maleic anhydride. Maleic anhydride is a solid at the conditions existing in knockout pot 116 and hence will be recovered here. Any water soluble impurities in the gaseous byproduct will be recovered in water scrubber 118 leaving a byproduct gaseous stream containing carbon monoxide, carbon dioxide and unreacted hydrocarbon. Analysis of a sample of this gaseous byproduct is gas chromatograph 126 will specify the amounts of carbon monoxide, carbon dioxide and unreacted hydrocarbon in this sample, and this information, together with the known amount of hydrocarbon in the feed gas will enable both the conversion (i.e. what percentage of the total hydrocarbon reactant was reacted) and the selectivity (i.e. the proportion of desired product produced vis a vis byproducts) to be obtained by simple calculation. Most preferably, this simple calculation can be done by a computer incorporated into control system 128 so that ultimate data of interest, the conversion and selectivity properties of each catalyst, can be directly recovered.

The inventive automatic catalyst screening unit has been found to be of great value in the rough screening of potential catalysts for various reactions. It has been designed to be simple in construction and operation yet provide valuable information to persons skilled in the art of catalysis. Moreover, the simple construction of the inventive screening unit makes it inexpensive to build and use as well as capable of operating with a minimum of down time due to hardware problems.

An important feature of the inventive screening unit is the design of reactor module 25. The reaction products of many catalytic reactions contain condensable and/or polymerizable materials. In view of the very small flow rates and reaction chambers employed in the inventive apparatus, such condensable and/or polymerizable ingredients could create a significant clogging problem if they were allowed to collect on operating hardware such as valves and the like. To this end, reactor module 25 of the inventive apparatus is provided with a common outlet manifold for receiving the reaction product passing out of each reaction chamber. Since actuator valve 27 will prevent essentially all flow of gases through any reaction chamber other than the reaction chamber to which gases are being fed, and since the common manifold is swept with the gross reaction product of the reaction chamber being used for a significant period of time before a sample is taken, a valving system at the outlet of reactor module 124 would not significantly improve the accuracy of the testing procedure accomplished by the inventive screening unit. Since it is the byproduct gases, not the desired reaction product, which are analyzed in the gas chromatograph in the preferred embodiment of the invention, and since the object of the inventive apparatus is to provide a rough screening of potential catalysts rather than exhaustive accurate data regarding one catalyst, the slight loss of accuracy if any due to the common manifold is more than compensated for by the freedom from plugging and low cost of the device.

Although only a single embodiment of the present invention has been described above, it should be appreciated that many changes and modifications can be made without departing from the spirit and scope of the invention. All such modifications are intended to be included within the scope of the present invention, which is to limited only by the following claims.

We claim:

1. A automatic catalyst screening unit for automatically screening a plurality of potential catalysts comprising:
   a reactor module comprising means defining a plurality of chambers having essentially equal volumes for receiving respective potential catalysts, each of said chambers having an inlet and an outlet;
   first heating means for heating potential catalysts when received in said chambers to the same temperature;

first control means for controlling said first heating means;

feeding means for feeding said at least one gaseous reactant to said plurality of chambers;

selector valve means intermediate said feeding means and said plurality of chambers for selectively placing only one of said chambers in fluid communication with said feeding means at any one time;

analyzing means for analyzing the product passing out of said plurality of chambers;

means defining a common manifold attached to the outlets of said plurality of chambers so that each of said chambers is in constant fluid communication with said manifold; and second control means for controlling said first control means, said selector valve means and said analyzing means so that (1) said at least one gaseous reactant is sequentially fed to said plurality of chambers in a predetermined sequence at at least one predetermined temperature and (2) gross product passing out of each of said chambers is fed to said analyzing means via said common manifold means and analyzed for useful product.

2. The unit of claim 1 wherein said plurality of chambers are elongated and essentially parallel, wherein first heating means includes an elongated heating element arranged parallel to said elongated chambers, and wherein said elongated chambers are arranged in annular configuration around said elongated heating element.

3. The unit of claim 2 wherein said first heating means further includes a second heating element annular in configuration and arranged around said elongated chambers.

4. The unit of claim 2 wherein said chambers are vertically oriented.

5. The unit of claim 2 further comprising second heating means intermediate said feeding means and said selector value means for heating reactant fed to said plurality of chambers.

6. The unit of claim 5 wherein said feeding means comprises a plurality of gas supply systems for independently supplying a plurality of gaseous reactants to said selector valve means.

7. The unit of claim 6 wherein a first gas supply system for controlling the flow of a first gaseous reactant to said selector valve means comprises first flow measuring means, first valve means for controlling the flow of said first gaseous reactant through said first flow measuring means, first conduit means for transferring said first gaseous reactant from said first flow measuring means to said selector valve means, waste conduit means attached to said first conduit means for transferring said first gaseous reactant from said flow measuring means to waste and second and third valve means connected to said first and waste conduit means, respectively, downstream of the junction of said first and waste conduit means for controlling the relative amounts of first gaseous reactant fed to said selector valve means and to waste.

8. The unit of claim 7 wherein a second supply system for controlling the flow of a second gaseous reactant to said selector valve means comprises second flow measuring means, fourth valve means for controlling the flow of said second gaseous reactant through second flow measuring means and second conduit means for transferring said second gaseous reactant from said second flow measuring means to said selector valve means by a flowpath bypassing said waste conduit means.

9. The unit of claim 8 wherein a third supply system comprises third flow measuring means for measuring the flow of second gaseous reactant passing therethrough, fifth valve means controlling the flow of second gaseous reactant through said third flow measuring means, and third conduit means for transferring second gaseous reactant from said third flow measuring means to said first conduit means upstream of the junction of said first conduit means with said waste conduit means.

10. The apparatus of claim 6 wherein said feeding means comprises a hydrocarbon supply system, an ammonia supply system and an air supply system for independently supplying hydrocarbon, ammonia and air, respectively, to said selector valve means; and wherein said hydrocarbon supply system comprises a hydrocarbon flow measuring means, a first valve for controlling the flow of hydrocarbon through said hydrocarbon flow measuring means, means defining a hydrocarbon flowpath for transferring hydrocarbon from said hydrocarbon measuring means to said selector valve means, waste conduit means connected to said hydrocarbon flowpath for transferring a portion of the hydrocarbon flowing through said hydrocarbon flowpath to waste, and a valve connected to each of said waste conduit means and said hydrocarbon flowpath downstream of the junction of said waste conduit means and said hydrocarbon flowpath for controlling the relative amounts of hydrocarbon fed to said selector valve means and to waste;

said ammonia supply system comprises ammonia flow measuring means, second valve means for controlling the flow of ammonia through said ammonia flow measuring means, and second conduit means for transferring ammonia passing through said ammonia flow measuring means to said selector valve means by a flowpath bypassing said waste conduit means; and wherein said air supply system comprises first, second and third air flow measuring means arranged in parallel, said first air flow measuring means being connected to said selector valve means by a flowpath bypassing said waste conduit means, said second air flow measuring means being connected to said second conduit means for mixing air with ammonia fed to said selector valve means via said second conduit, and said third air flow measuring means being connected to said hydrocarbon flowpath upstream of said junction for mixing air with hydrocarbon fed to said selector valve means upstream of said junction.

11. The unit of claim 2 wherein said heating module comprises a block, wherein said elongated chambers comprise essentially cylindrical holes in said block, and wherein said elongated heating element is received in and integral with said block.

12. The unit of claim 2 further comprising second heating means between said feeding means and said selector valve means for heating said at least one gaseous reactant to a predetermined temperature.

13. The unit of claim 12 further comprising third control means for controlling said second heating means, said third control means being controlled by said second control means.

14. The apparatus of claim 2 wherein said analyzing means includes a gas chromatograph.

15. The apparatus of claim 14 wherein said analyzing means includes a sampling system for recovering a sample of the gas to be analyzed and transferring said sample to said gas chromatograph, said second control means controlling said sampling system and said gas chromatograph so that for each gross product produced a sample of the gas to be analyzed is recovered and analyzed.

16. The apparatus of claim 15 further comprising vent means for venting gas passing out of said reactor module, said second control means controlling said vent means so that for each test run of said screening unit gas to be analyzed is passed through said sampling system only after a predetermined period of time.

17. The unit of claim 16 further comprising recovery means between said reactor module and said sampling system for recovering from said gross product components thereof which would clog said gas chromatograph.

18. The apparatus of claim 17 wherein said recovery means comprises means for recovering solid and liquid components of said gross product, means for recovering water soluble components of said gross product and means for recovering water vapor from said gross product.

19. Automatic catalyst screening unit comprising: a reactor module defining a plurality of elongated reaction chambers for receiving respective potential catalysts; feeding means for individually and selectively feeding each of said reaction chambers with gaseous reactant; and analyzing means for analyzing the product passing out of said reaction chambers, said analyzing means communicating with said plurality of reaction chambers by means of a common manifold.

20. A reactor module for testing a plurality of potential catalysts comprising a solid block; an elongated heating element received in and integral with said block, said block defining a plurality of elongated, essentially parallel, reaction chambers arranged in an annular configuration around said elongated heating element; and means defining a common manifold in constant fluid communication with each of said reaction chambers.

* * * * *